United States Patent [19]
Cosmescu

[11] Patent Number: 5,431,650
[45] Date of Patent: Jul. 11, 1995

[54] VORTEX HAND PIECE SHROUD FOR AUTOMATIC SMOKE EVACUATOR SYSTEM FOR A SURGICAL LASER APPARATUS AND METHOD THEREFOR

[76] Inventor: Ioan Cosmescu, 14449 No. 22nd St., Phoenix, Ariz. 85022

[21] Appl. No.: 196,802

[22] Filed: Feb. 15, 1994

Related U.S. Application Data

[63] Continuation of Ser. No. 989,238, Dec. 11, 1992, abandoned.

[51] Int. Cl.⁶ .............................................. A61B 17/39
[52] U.S. Cl. ........................................ 606/41; 606/13; 606/45; 604/22
[58] Field of Search ................................. 606/41–49, 606/13; 604/21, 22

[56] References Cited

U.S. PATENT DOCUMENTS

| | | | |
|---|---|---|---|
| 4,719,914 | 1/1988 | Johnson | 606/49 |
| 4,850,352 | 7/1989 | Johnson | 604/35 |
| 5,055,100 | 10/1991 | Olsen | 604/22 |
| 5,154,709 | 10/1992 | Johnson | 606/45 |
| 5,181,916 | 1/1993 | Reynolds et al. | 604/22 |
| 5,192,267 | 3/1993 | Shapira et al. | 604/22 |

*Primary Examiner*—Stephen C. Pellegrino
*Assistant Examiner*—Michael Peffley
*Attorney, Agent, or Firm*—Harry M. Weiss

[57] ABSTRACT

A electrosurgical unit (ESU) apparatus is disclosed in which an improved handpiece and smoke evacuation shroud apparatus and method provides efficient smoke collection without obstructing the surgeon's view of the surgical site through use of a smoke evacuation shroud design which controls the velocity and direction of the evacuating air flow in the vicinity of the surgical site by forming a vortex. This vortex creates a "funnel cloud" type action like that of a tornado or cyclone which contains the smoke immediately as it is generated by the cutting and coagulating action of the operating tip of the ESU surgery handpiece. The action of this vortex is a key advantage of the invention since generated smoke is immediately contained, and removed thereby avoiding obstructing the view of the surgeon.

2 Claims, 2 Drawing Sheets

VORTEX HAND PIECE SHROUD FOR AUTOMATIC SMOKE EVACUATOR SYSTEM FOR A SURGICAL LASER APPARATUS AND METHOD THEREFOR

This is a continuation of application Ser. No. 07/989,238 filed on Dec. 11, 1992, abandoned.

BACKGROUND OF THE INVENTION

Related Application

This patent application is related to my U.S. Pat. No. 5,108,389 entitled "AUTOMATIC SMOKE EVACUATOR ACTIVATOR SYSTEM FOR A SURGICAL LASER APPARATUS AND METHOD THEREFOR", filed May 23, 1990, and is incorporated by reference thereto.

This patent application is also related to my co-pending patent application entitled "RADIO FREQUENCY SENSOR FOR AUTOMATIC SMOKE EVACUATOR SYSTEM FOR A SURGICAL LASER AND/OR ELECTROSURGICAL APPARATUS AND METHOD THEREFOR" which is being simultaneously filed with the present application and is incorporated by reference thereto.

This patent application is also related to my patent application entitled "AUTOMATIC EVACUATOR SYSTEM FOR A SURGICAL LASER APPARATUS AND METHOD THEREFOR" that was filed on Sep. 24, 1991 as a Continuation-In-Part patent application of patent application Ser. No. 07/527,589 which has issued (as identified above) as U.S. Pat. No. 5,108,389.

1. Field of the Invention

This invention refers in general to automatic smoke evacuator systems and methods therefor for a laser surgical and electrosurgical unit (ESU) and, in particular, to apparatus and methods therefor for the hand piece and smoke evacuation shroud arrangements used in such a laser surgical and electrosurgical unit (ESU).

2. Description of the Prior Art

In the past, a surgical laser apparatus utilized a smoke evacuator system which was manually turned on and off, but which was generally continuously operated during a surgical laser procedure (laparotomy). A smoke evacuator system functioned as part of a surgical laser and ESU apparatus. The smoke evacuator systems of many surgical laser and ESU apparatus produced a constant noise during its use or operation, used a high amount of electrical energy and the continuous air pressure on the filter element of the smoke evacuator systems of the surgical laser and ESU apparatus usually saturated or overloaded the system's filter thereby increasing the risk of allowing toxic fumes which were supposed to be evacuated from the surgical area to escape uncontrolled into the medical operating room rather than being vented outside in accord with the intended function of the smoke evacuator system. Further, for safety purposes, the FDA does not allow any device to be in electrical contact with the control circuitry of a surgical laser. Therefore, there was clearly great benefit to the surgeon and to the operating room staff if the smoke evacuator systems of the surgical laser and ESU apparatus was activated only during the period of time the laser surgical and ESU apparatus was actually in operation. My U.S. Pat. No. 5,108,389 provides a solution to these problems of past systems by providing an automatic smoke evacuator system in which the required activation of the smoke evacuator is initiated by the interruption of a beam of electromagnetic radiation. In the preferred embodiment, the beam of electromagnetic radiation is an infrared beam which is interrupted by a foot switch which is coupled to the laser ESU and which controls its actuation. As is described in U.S. Pat. No. 5,108,389, this system greatly improves the safety and effectiveness of the operating environment for laser surgical and ESU procedures and has provided great benefit in it use. As additional experience has been obtained in the use of this system, the possibility for the improved and more effective operation of the laser surgery and electrosurgery handpiece and its associated smoke evacuator shroud has emerged.

In order to evacuate the smoke from the surgical field in laparotomy when an ESU handpiece is used for cutting and coagulation, several methods have been used which functioned but which had a low efficiency. In order to be efficient, the shroud which performs the smoke collection function must be as close as possible to the operating tip of the handpiece where the smoke is generated. The problem with prior apparatus and methods was that arrangements for smoke collection which were more efficient tended to obstruct the view of the surgeon making use of the handpiece very difficult. Accordingly, there was a need for an improved handpiece and shroud arrangement which provided for efficient smoke collection without obstructing the surgeon's view of the surgical site.

SUMMARY OF THE INVENTION

An object of this invention is to provide an improved handpiece and smoke evacuation shroud apparatus and method for either a laser surgical and electrosurgical unit.

Another object of this invention is to provide an improved handpiece and smoke evacuation shroud apparatus and method for either a laser surgical and electrosurgical unit in which the smoke evacuation shroud provides efficient smoke collection without obstructing the surgeon's view of the surgical site.

Another object of this invention is to provide an improved handpiece and smoke evacuation shroud apparatus and method for either a laser surgical and electrosurgical unit in which the smoke evacuation shroud provides efficient smoke collection without obstructing the surgeon's view of the surgical site by designing the smoke evacuation shroud to control the velocity and direction of the evacuating air flow in the vicinity of the surgical site by forming a vortex.

According to the present invention, a laser surgical or electrosurgical apparatus is provided in which an improved handpiece and smoke evacuation shroud apparatus and method provides efficient smoke collection without obstructing the surgeon's view of the surgical site through use of a smoke evacuation shroud design which controls the velocity and direction of the evacuating air flow in the vicinity of the surgical site by forming a vortex.

The foregoing and other objects, features and advantages of the present invention, as well as details of the preferred embodiment thereof, will be more fully understood from the following description and drawing.

DESCRIPTION OF THE PREFERRED EMBODIMENT

Figure 3:
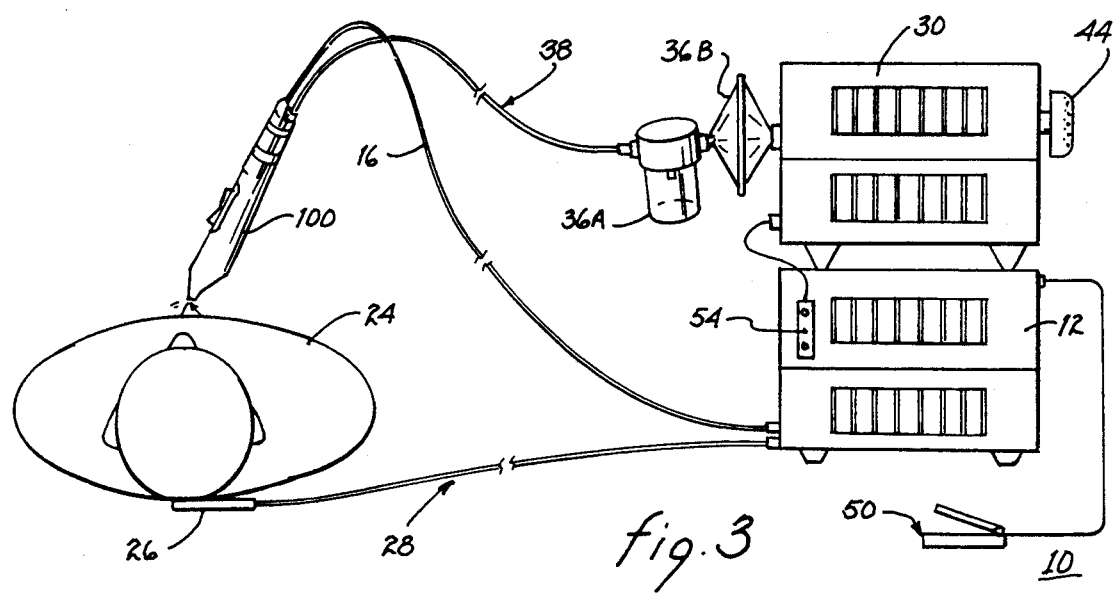
FIG. 3 is a pictorial diagram of an ESU system using the surgery handpiece and smoke evacuation shroud assembly of the present invention.

FIG. 3 is a pictorial diagram of an ESU system using the electrosurgery unit (ESU) handpiece and smoke evacuation shroud assembly of the present invention. FIG. 3 is related to the FIG. 1 system block diagram of my co-pending patent application entitled "RADIO FREQUENCY SENSOR FOR AUTOMATIC SMOKE EVACUATOR SYSTEM FOR A SURGICAL LASER AND/OR ELECTROSURGICAL APPARATUS AND METHOD THEREFOR" which is being simultaneously filed with the present application and which has been incorporated by reference above. Thus the FIG. 3 pictorial diagram includes a laser electrosurgical unit (ESU) 12, output path 16, patient 24, patient ground plate 26, patient ground return path 28, smoke evacuator unit 30, line filter and fluid trap 36A and 36B, smoke evacuation channel 38, vent filter 44, foot switch sensor means 50 and RF sensor 54 all of which are interconnected and which function as described in detail in the co-pending application to create the system environment in which the surgery handpiece and smoke evacuation shroud assembly 100 functions as shown in FIG. 3 and which is described in greater detail below.

Figure 1:
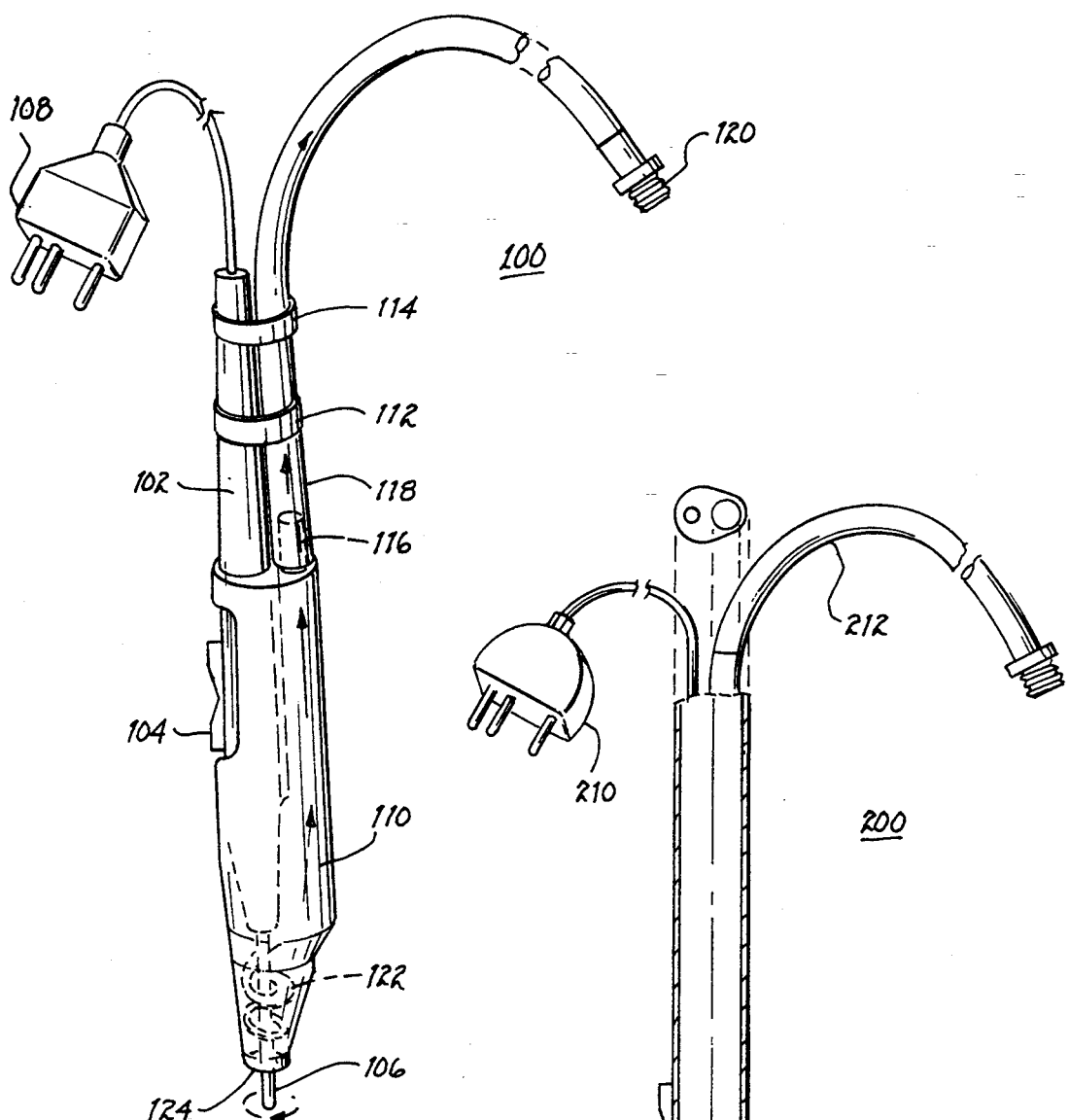
FIG. 1 is a electrosurgery unit (ESU) handpiece and smoke evacuation shroud assembly according to the present invention.

FIG. 1 shows a ESU surgery handpiece and smoke evacuation shroud assembly 100 according to the present invention. In FIG. 1, a conventional electrosurgery handpiece 102 which has a manual operating switch 104, an operating tip 106 and which couples to an interconnecting plug 108 is used. Electrosurgery handpiece 102 is mounted in and surrounded by smoke evacuation shroud 110 which is adapted to form an air-tight seal around the electrosurgery handpiece 102 and which is held in place by mounting rings 112 and 114. Smoke evacuation shroud 110 also includes a coupling 116 which couples it to a smoke evacuation channel 118 which in turn couples to a fitting 120 which is adapted for attachment to the smoke evacuation unit of the previously described system 10. A key feature of smoke evacuation shroud 110 is vortex generating means 122 which is formed inside smoke evacuation shroud 110 in the region where the shroud surrounds operating tip 106 of electrosurgery handpiece 102. Vortex generating means 122 is a spiral vane structure which is of a size and shape to cause the air and smoke flowing into the opening 124 of smoke evacuation shroud 110 to form a vortex. This vortex creates a "funnel cloud" type action like that of a tornado or cyclone which contains the smoke immediately as it is generated by the cutting and coagulating action of operating tip 106 of electrosurgery handpiece 102. The action of this vortex is a key advantage of the present invention in that since generated smoke is immediately contained, it does not obstruct the view of the surgeon. The size of opening 124 and the size and shape of vortex generating means 122 can be changed to control the vortex as required by the application.

Figure 2:
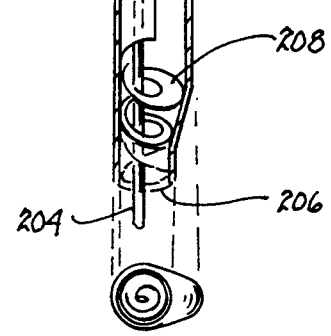
FIG. 2 is an alternative embodiment of a electrosurgery unit (ESU) handpiece and smoke evacuation shroud assembly according to the present invention.

FIG. 2 is an alternative embodiment of a electrosurgery handpiece and smoke evacuation shroud assembly 200 according to the present invention. In this embodiment, an integrated shroud handpiece assembly 202 is formed as a single unit so that an operating tip 204 and a shroud opening 206 are all formed as part of the same unit which includes a vortex generating means as part of its internal structure. Except for the fact that it is formed as a single integrated structure, the structure and function of integrated shroud-handpiece assembly 202, which includes coupling to an interconnecting plug 210 and smoke evacuation channel 212, ie the same as previously described for the embodiment of FIG. 1.

Figure 4A:
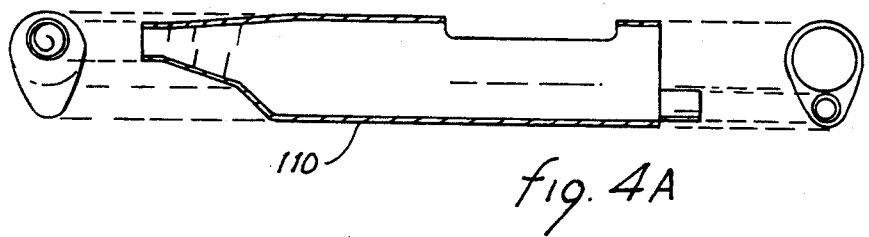
FIG. 4A is a cross-sectional view of the smoke evacuation shroud portion of the assembly of FIG. 1.
Figure 4B:
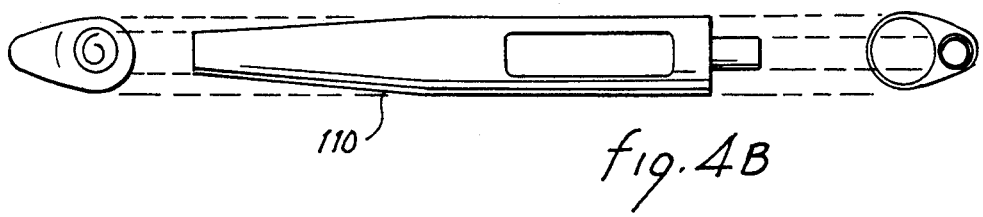
FIG. 4B is a top view of the smoke evacuation shroud portion of the assembly of FIG. 1.
Figure 4C:
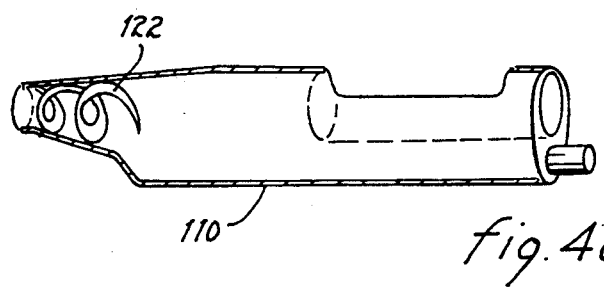
FIG. 4C is an isometric cross-sectional view of the smoke evacuation shroud portion of the assembly of FIG. 1.
Figure 5:
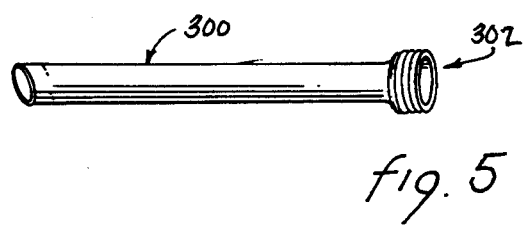
FIG. 5 is a perspective view of an extension tubular member that is attachable to the end of the smoke evacuation shroud portion of the assembly of FIG. 1.

Additional cross-sectional and isometric views of the FIG. 1 smoke evacuation shroud 110 with vortex generating means 122 are shown by FIGS. 4A, 4B and 4C. FIG. 5 depicts an extension tubular member 300 that can be rapidly attached or detached, by means of threads 302 located at one of the tubular member 300, to the end of the smoke evacuation shroud portion of the assembly of FIG. 1 to provide an extended or longer portion for use with long ESU tips while the invention has been particularly shown and described with reference to a preferred embodiment thereof, it will be understood by those skilled in the art that changes in form and detail may be made therein without departing from the spirit and the scope of the invention. For example, while the embodiment depicted in the drawings is directed to an ESU apparatus, a laser surgical apparatus that generates a surgical RF can also be used with the smoke evacuator shroud and system depicted herein.

I claim:

1. A electrosurgical unit (ESU) apparatus comprising, in combination:
   a removable elongated shroud, adaptably fitted over the external surface of an electrosurgical unit;
   electrosurgical means located within a portion of said shroud and having electrosurgical tip means that extends below an opening located at a distal portion of said shroud for use in surgery;
   conduit means located within said elongated shroud having a narrow portion surrounding a portion of said electrosurgical means and in communication with said opening at the distal portion of said elongated shroud and an enlarged portion extending proximally from said portion of said electrosurgical means and said tapered portion to a proximal opening in said elongated shroud for both increasing suction of smoke from said opening located at the distal portion of said shroud upwardly to said proximal opening in said elongated shroud and increasing visibility of said tip means below said opening in the distal portion of said shroud to permit better visualization of the surgery;
   external conduit means coupled to said proximal opening in said elongated shroud for exhausting smoke located within said shroud;
   smoke evacuation means coupled to said external conduit means for exhausting smoke passing from said conduit means into said external conduit means; and vortex means located within a portion of said elongated shroud and comprising a spiraling vane structure having said tapered first radius near said opening of said distal portion of said elongated shroud and having a second radius located above said first radius, said second radius being larger than said first radius;

said elongated shroud having a switch access opening located between said opening located at said distal portion of said elongated shroud and said proximal opening, said switch access opening permitting the operation of a control switch of said electrosurgical means extending through said switch access opening.

2. A laser surgical unit apparatus comprising, in combination:

a removable elongated shroud, adaptably fitted over the external surface of a laser surgical unit;

laser source means located within a portion of said shroud for generating outwardly of an opening located at a distal portion of said shroud a laser beam for use in surgery;

conduit means located within said elongated shroud having a tapered portion surrounding a portion of said laser source means and in communication with said opening at the distal portion of said elongated shroud and an enlarged portion extending proximally from said portion of said laser source means and said tapered portion to a proximal opening in said elongated shroud for both increasing suction of smoke from said opening located at the distal portion of said shroud upwardly to said proximal opening in said elongated shroud and increasing visibility of the beam below said opening in the distal portion of said shroud to permit better visualization of the surgery;

external conduit means coupled to said proximal opening in said elongated shroud for exhausting smoke located within said shroud;

smoke evacuation means coupled to said external conduit means for exhausting smoke passing from said conduit means into said external conduit means; and vortex means located within said tapered portion of said elongated shroud and comprising a spiraling vane structure having a first radius near said opening of said distal portion of said elongated shroud and having a second radius located above said first radius, said second radius being larger than said first radius;

said elongated shroud having a switch access opening located between said opening located at said distal portion of said elongated shroud and said proximal opening, said switch access opening permitting the operation of a control switch of said laser source means extending through said switch access opening.

* * * * *